US00PP10352P

United States Patent [19]

Saville

[11] Patent Number: Plant 10,352

[45] Date of Patent: Apr. 28, 1998

[54] MINATURE ROSE PLANT NAMED 'SAVINN'

[75] Inventor: F. Harmon Saville, Newburyport, Mass.

[73] Assignee: Nor'East Miniature Roses, Inc., Rowley, Mass.

[21] Appl. No.: 787,233

[22] Filed: Jan. 22, 1997

[51] Int. Cl.[6] ..... A01H 5/00

[52] U.S. Cl. ..... Plt./8.1

[58] Field of Search ..... Plt./8.1, 7.1

*Primary Examiner*—Howard J. Locker

*Attorney, Agent, or Firm*—Christie, Parker & Hale, LLP

[57] ABSTRACT

A new miniature rose with white flowers.

1 Drawing Sheet

BACKGROUND OF THE INVENTION

The present invention relates to a new and distinct variety of rose plant of the miniature rose class, which was created by crossing as seed parent the variety known as 'Savajinks' (U.S. Plant Pat. No. 8,412) and as pollen the variety known as 'Savalife' (U.S. Plant Pat. No. 5,482). The varietal denomination of this new rose is 'Savinn'.

SUMMARY OF THE INVENTION

Among the novel characteristics possessed by this new variety which distinguishes it from its parents and all other varieties of which I am aware is its attractive many petaled white flowers borne on a plant with attractive green foliage. The plant has a vigorous, well branched spreading growth habit that makes it useful in landscaping. Flower color tends to ivory in cool weather and to pure white in full sun.

The new variety resembles 'Savalife' in form and fullness but not in color. Its habit is similar to 'Savajinks' but differs in flower color.

Asexual reproduction by propagation of vegetative cuttings of the new variety as performed in Essex County, Mass. shows that the foregoing and other distinguishing characteristics come true to form and are established and transmitted through succeeding propagations.

BRIEF DESCRIPTION OF ILLUSTRATION

The accompanying illustration shows typical specimens of the flowers of the new variety in different stages of development depicted in color as nearly true as it is reasonably possible to make the same in a color illustration of this character.

DETAILED DESCRIPTION OF THE NEW VARIETY the following is a detailed description of my new variety, with color terminology in accordance with The Royal Horticultural Society Colour Chart (R.H.S.C.C.). The terminology used in color description herein refers to plate numbers in the aforementioned color chart. Phenotypic expression may vary with light availability, environmental and cultural conditions.

Parentage:

*Seed parent.*—'Savajinks'.

*Pollen parent.*—'Savalife'.

Class: Miniature.

The following observations are made of specimens grown under plastic in Essex County, Mass., during October.

FLOWER

Blooming habit: Continuous.

A. Bud:

(1) *Size.*—Small.

(2) *Form.*—Oval, pointed at apex.

(3) *Color.*—As sepals divide, bud color is near 4D.

(4) *Sepals.*—Three outer sepals heavily bearded; usually inner most sepals finely bearded; longer than the bud; color between 144A and 144B, spread to horizontal as blooms open. Drop with last petals.

(5) *Peduncle.*—Length — average about 1⅛ to 1¾ inch. Aspect — slightly curved. Strength — erect. Color — near 144B flushed with near 183B where exposed to sun.

B. Bloom:

(1) *Size.*—Average size when fully expanded up to about 1½ inches.

(2) *Borne.*—Singly.

(3) *Form.*—High centered at first becoming flat; petals become loosely rolled outward and ruffled at maturity.

(4) *Petalage.*—Number of petals under normal conditions about 38 to 50.

(5) *Color.*—After sepals divide near 4D; when petals begin to unfurl near 4D at base becoming white at outer edges; when ½ open near 4C at base, becoming white at outer edges on top surface, near 4D at base becoming white at outer edges on under surface; inner petals near 4D with white only at edges on top surface, near 4D at base, remainder white at under surface.

(6) *Color change.*—General tonality — white. As bloom ages, color changes a mix of near 4D and white to mostly all white. The general tonality becomes a mix of ivory and white becoming whiter after three or more days.

C. Petals:

(1) *Texture.*—Medium.

(2) *Appearance.*—Inside and outside satiny.

(3) *Form.*—Outer petals broad fan shaped and reflex to points; inner petals ovoid, and curl under.

(4) *Arrangement.*—Outer petals imbricated, inner petals may be 3 or 4 together, one in front of another.

(5) *Petaloids in center.*—Variable, many, average 16.

(6) *Persistence.*—Drop off cleanly in 5–9 days.

(7) *Fragrance.*—None.

(8) *Lasting quality.*—About 5–9 days on the plant; about 5–9 days as a cut flower.

REPRODUCTIVE ORGANS

A. Stamens, filaments and anthers:

*Arrangement.*—Sometimes mixed with petaloids.

B. Stamens:
*Quantity.*—About 0 to 20.
C. Filaments:
*Approximate length.*—Uneven in length, up to about 1/8 inches long.
*General color.*—Near 4D.
D. Anthers:
*Color.*—White to near 4D.
E. Pollen:
*Color.*—Near 17A.
*Quantity.*—Small amount.
F. Pistils:
*Quantity.*—Very few, less than about 20.
G. Styles: Uneven.
*Color.*—Near 39A.
H. Stigmas:
*Color.*—White.
I. Hips:
*Shape.*—None observed.

PLANT

A. Form: Upright, spreading.
B. Growth: Vigorous.
*Height.*—About 30 inches high and wide.
C. Foliage: Compound of 5–7 leaflets, occasionally 3.
*Size.*—Medium.
*Quantity.*—Abundant.
*Color.*—New Foliage: Upper side between near 144A and 146A; under side near 146B flushed with near 176B. Old Foliage: Upper side near 147A; under side near 148B flushed with near 176A.
*Shape.*—Oval, pointed.
*Texture.*—Upper side semiglossy; underside matte.
*Thorns of prickles.*—Very few, 1 to 3 on underside of leaf.
*Edge.*—Serrated.
*Serration.*—Nearly even, fine at tip to nearly smooth at base.
*Leaf stem.*—New — near 177A; underside near 144C flushed with near 177A. Old — topside near 146B; edges of 147A; underside near 146D.
*Stipules.*—Very lightly bearded.
*Resistance to diseases.*—Blackspot Average. Mildew Average. Rust Average.
D. Wood:
*New wood.*—Color near 183D to 187B; bark smooth.
*Old wood.*—Color between near 146A and near 147B with strips of near 165C, slightly raised; bark nearly smooth.
E. Thorns:
*Quantity.*—Very few on main stalk and laterals.
*Form.*—Straight, occasionally curving down.
*Length.*—Less than about 5/16 inch.
*Color.*—Near 183B, some 184B and some 183A.
*Position.*—Irregular.
F. Prickles:
*Main stalk.*—None.
*Laterals.*—None.
*Leaves.*—Usually about 1 to 3 prickles on underside at leaf stems.
G. Winter hardiness: Needs protection in severe climate, tested hardy to zone 4.

I claim:

1. A new and distinct variety of rose plant of the miniature rose class, substantially as shown and described.

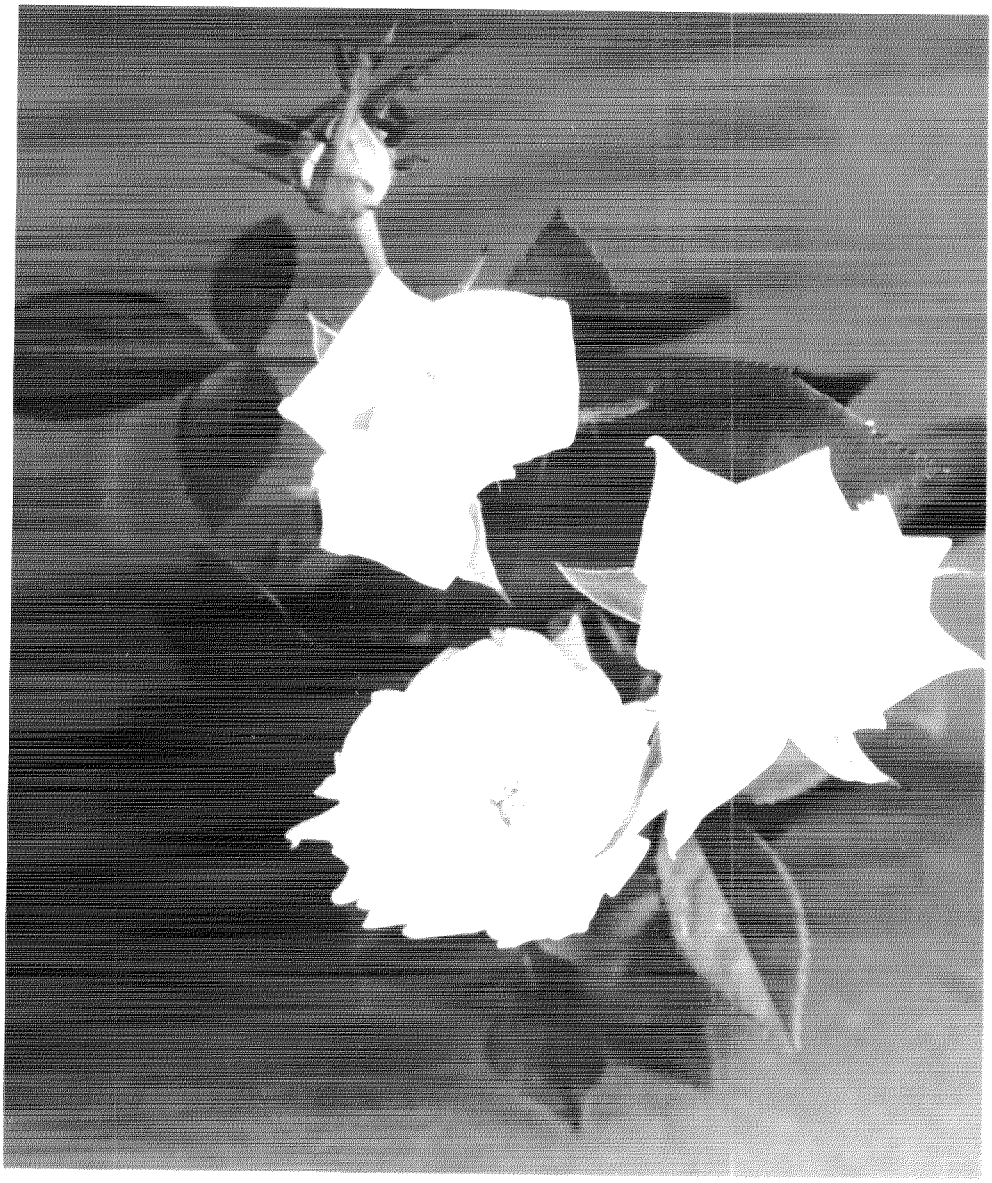

* * * * *